(12) United States Patent
Shah et al.

(10) Patent No.: US 9,011,705 B2
(45) Date of Patent: Apr. 21, 2015

(54) METHOD OF FORMING A POLYMER SUBSTRATE WITH VARIABLE REFRACTIVE INDEX SENSITIVITY

(75) Inventors: Kwok Wei Shah, Singapore (SG); Xiaodi Su, Sinagpore (SG); Soo Jin Chua, Singapore (SG); Hong Yee Low, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/559,533

(22) Filed: Jul. 26, 2012

(65) Prior Publication Data

US 2013/0295325 A1 Nov. 7, 2013

(30) Foreign Application Priority Data

Jul. 28, 2011 (SG) .................. 201105455

(51) Int. Cl.
*B44C 1/22* (2006.01)
*G01N 21/552* (2014.01)

(52) U.S. Cl.
CPC .............. *G01N 21/554* (2013.01); *B44C 1/227* (2013.01); *Y10S 977/888* (2013.01)

(58) Field of Classification Search
CPC ........ B81C 1/0046; B29C 59/14; B44C 1/22; B44C 1/227
See application file for complete search history.

(56) References Cited

FOREIGN PATENT DOCUMENTS

WO WO2009022985 * 2/2009 ............. G01N 21/55

OTHER PUBLICATIONS

Y-C. Lee et al., "Micro-/Nano-Lithography Based on the Contact Transfer of Thin Film and Mask Embedded Etching" J. Micromech. Microeng. vol. 18, year 2008, pp. 1-7.*
T.J. Johnson et al., "Laser Modification of Preformed Polymer Microchannels", Anal. Chem. vol. 73, year 2001, pp. 3656-3661.*

* cited by examiner

*Primary Examiner* — Lan Vinh
*Assistant Examiner* — Jiong-Ping Lu
(74) *Attorney, Agent, or Firm* — Blakely, Sokoloff, Taylor & Zafman LLP

(57) ABSTRACT

The present invention relates to a method of forming polymer substrate with variable refractive index sensitivity, the method comprising the steps of: (a) contacting a metal-coated patterned mold with a polymer substrate at a temperature sufficient to deform said polymer substrate to thereby deposit a patterned mask of a metal film on the polymer substrate; and (b) etching away portions of said polymer substrate not covered by said patterned mask under conditions to form a region of variable refractive index sensitivity on said polymer substrate.

18 Claims, 12 Drawing Sheets

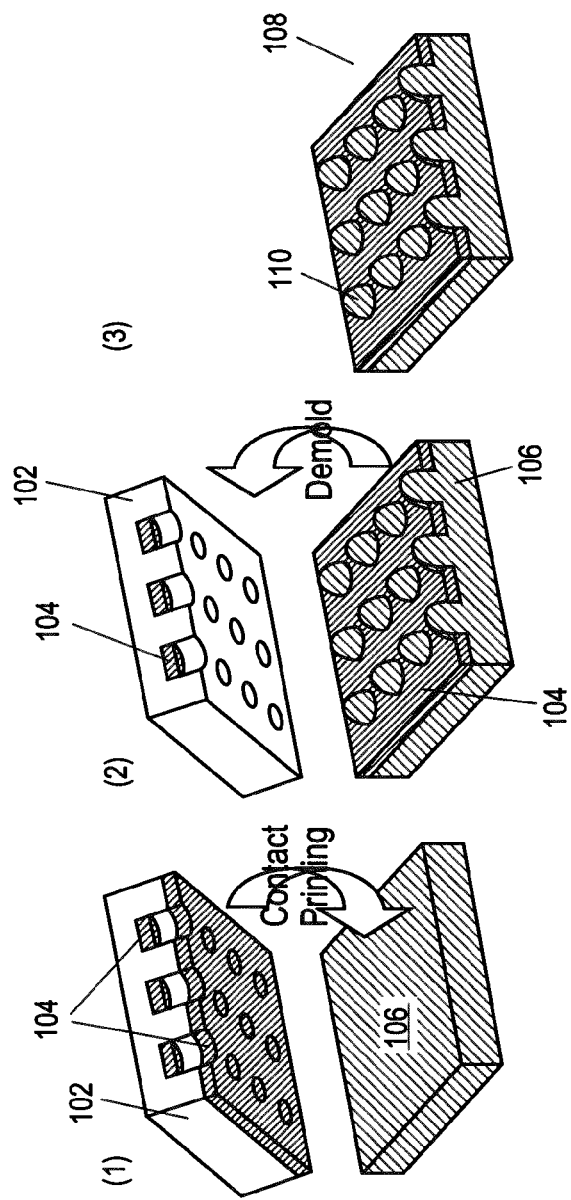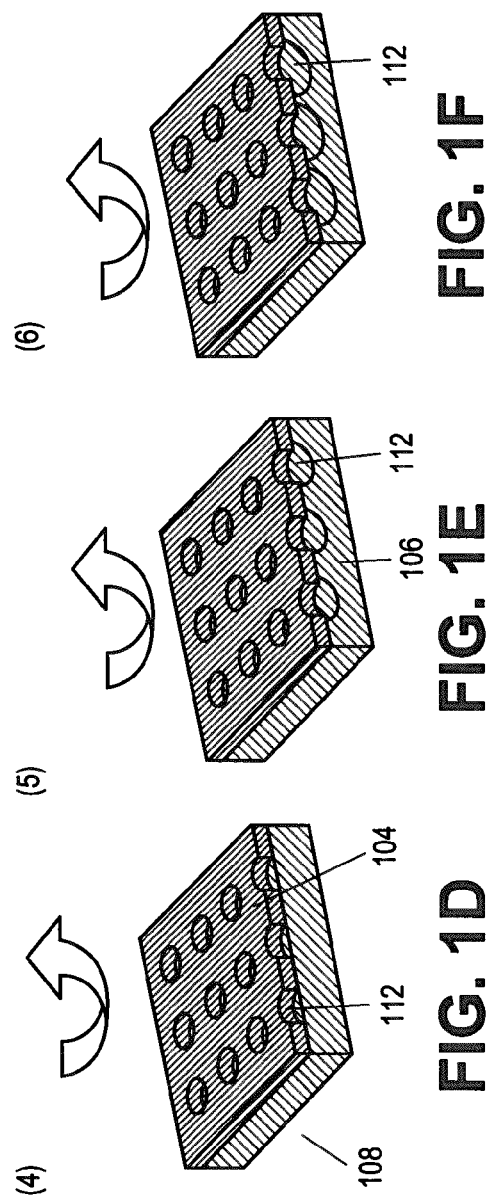

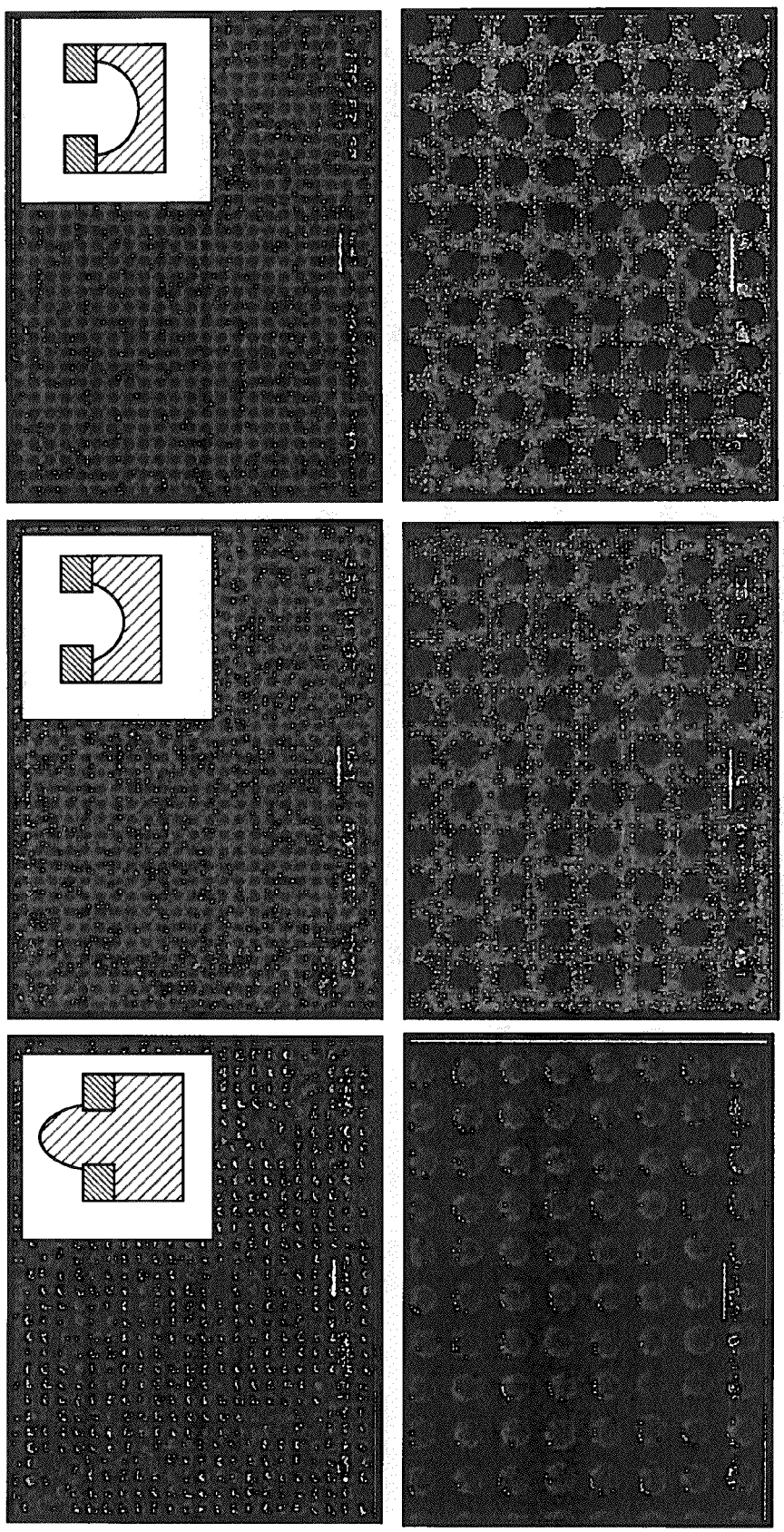

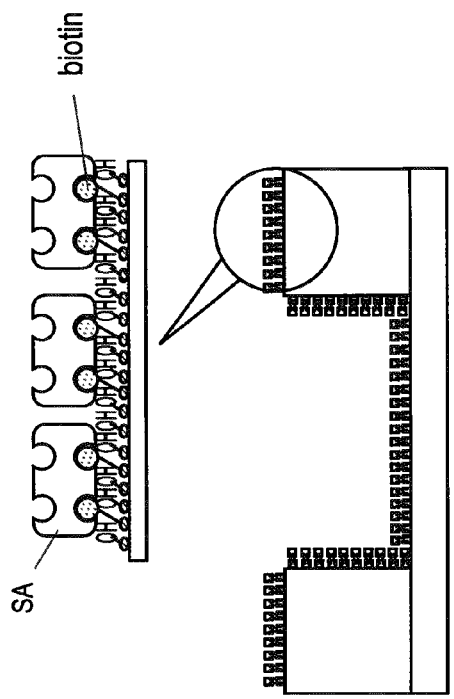
FIG. 12A
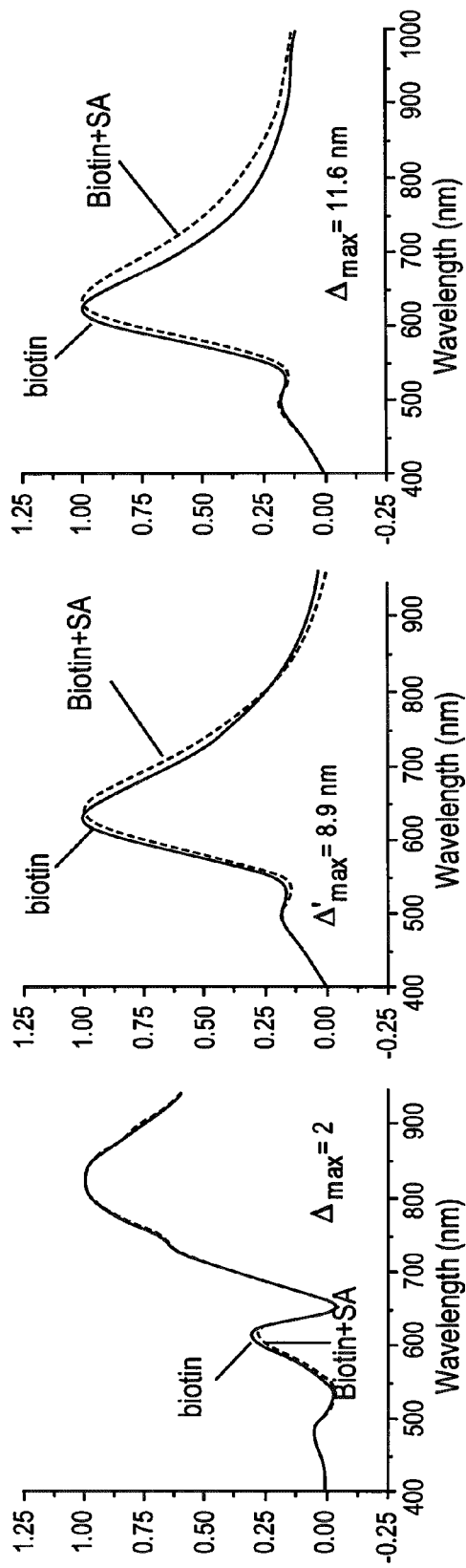
FIG. 12B
FIG. 12C
FIG. 12D

METHOD OF FORMING A POLYMER SUBSTRATE WITH VARIABLE REFRACTIVE INDEX SENSITIVITY

TECHNICAL FIELD

The present invention generally relates to a method of forming polymer substrates with variable refractive index sensitivity and uses of the polymer substrates thereof.

BACKGROUND

Surface Plasmon Resonance (SPR) refers to the collective oscillation of valence electrons of a solid upon being irradiated by photons generated by incident electromagnetic (EM) radiation. In particular, SPR refers to the resonance between the frequency of the EM photons and the natural frequency of the valence electrons which results in the resonant oscillation of the valence electrons. Where the SPR occurs in nano-sized structures, it is termed "Localized Surface. Plasmon Resonance" (LSPR). Notably, the SPR phenomena can be used for the detection of molecules which become adsorbed onto the surface of a said (e.g., a plasmon-active metal).

Accordingly, methods of fabricating substrates supporting a layer of plasmon-active metal film are of great interest, particularly in the field of chemical sensors and biosensors. For instance, it is known that an ordered array of nanostructures with gold films can directly convert incident light into surface plasmons (SPs), which can lead to enhanced optical transmission or extraordinary optical transmission (EOT). In some studies, nanohole arrays in a gold film have been used as biomolecular sensors to detect and study surface-binding interactions using the EOT phenomenon.

The key advantages of nanohole array-based plasmonic sensors over conventional prism- or grating-based SPR sensors are (1) the elimination of the need for a bulky prism, (2) simple light coupling instrumentation, (3) use of small reagent volumes, (4) high sensitivity, and (5) easy integration, miniaturization and multiplexing.

However, a significant obstacle faced by current nanohole array-based plasmonic sensors relates to the lack of fabrication techniques that are suitable for large output, large area (centimeter-scale) and low-cost production of plasmonic substrates with ordered nanoholes as sensing elements.

Nanohole arrays are commonly fabricated by beam-based techniques such as e-beam lithography (EEL) and focused ion beam (FIB). Despite having high resolution and control, these beam techniques are generally time-consuming and are limited by small throughput due to the serial nature of such lithography techniques. Additionally, these lithography techniques require sophisticated infrastructure and incur high capital costs. Accordingly, it is difficult to achieve a high throughput with large area fabrication using techniques such as EBL or FIB. As such, these techniques are not commercially feasible for large scale implementation.

Alternatively, other techniques such as nanoimprint (NIL) and nanosphere lithography (NSL) or colloidal lithography techniques have also been considered in the state of the art. NIL is capable of producing high-quality nanoholes on a wafer-scale, but requires multiple steps and expensive nanoimprinting equipment.

On the other hand, nanosphere lithography (NSL) employs self-assembled polystyrene/silica nanospheres as a lithographic mask to fabricate sub-wavelength patterns However, the NSL technique faces significant technical difficulty in achieving defect-free self-assembled colloidal spheres, which are typically larger than 100 μm. Hence, it follows that the NSL technique would encounter even greater difficulty in achieving a defect-free self-assembled monolayer of nano-sized structures.

Accordingly, there is a need to provide a method for providing e polymer substrate supporting a plasmon-active metal film that overcomes, or at least ameliorates, one or more of the disadvantages described above.

In particular, there is a need to provide a method for preparing a polymer substrate that can be used for SPR or LSPR applications, which is capable of high throughput, large surface area fabrication and is cost-effective to implement.

SUMMARY

In a first aspect, there is provided a method of forming a polymer substrate with variable refractive index sensitivity, the method comprising the steps of: (a) contacting a metal-coated patterned mold with a polymer substrate at a temperature sufficient to deform said polymer substrate to thereby deposit a patterned mask of a metal film on the polymer substrate; and (b) etching away portions of said polymer substrate not covered by said patterned mask under conditions to form a region of variable refractive index sensitivity on said polymer substrate.

Advantageously, the disclosed method presents a cost-effective approach for synthesizing plasmon-active polymer substrates of large surface area (at least in the centimeter scale) and which exhibits the following desirable attributes for LSPR applications:

(A) Physical Attributes:
  (1) highly-ordered array of nanostructures;
  (2) large patterned area; and
  (3) free-standing nanostructure.

(B) Functional Attributes:
  (1) optimized bulk refractive index sensitivity; and
  (2) adjustable/tunable wavelength and refractive index sensitivity.

(C) Fabrication Attributes:
  (1) facile and fast two-step fabrication method; and
  (2) no requirement for the provision of an adhesion layer between the Plasmon-active metal film and the polymer substrate (e.g., a chromium or titanium layer for improving gold-adhesion).

(D) Commercial Attributes:
  (1) low capital cost; and
  (2) high throughput possible.

In one embodiment, the contacting step (a) may be referred to as a microstamping or micro-contact printing (CP) step.

Advantageously, the contacting step (a) offers a simple, relatively quick and parallel fabrication of repetitive patterns over a large area, which negates the requirements of conventional methods, such as, the need for an expensive mask, wet-etching, photolithography or ion-beam lithography. Advantageously, by using a suitable mold, it is possible to fabricate nanostructures (e.g., nanoholes, nanoislands, nanopyramids, nanocones, etc) of varying shapes and geometry. Additionally, the speed and versatility of the contacting step (a) allows high-throughput production of a masked polymer substrate.

The etching step (b) is thereafter used to etch away portions of the polymer substrate not masked by the metal film to thereby form an ordered array of micro- or nanostructures on the polymer substrate. Advantageously, the etching step can be suitably controlled, together with other factors such as metal film thickness, to provide optimized/maximized bulk refractive index sensitivity. For example, the etching duration can be adjusted to provide shallow trenches, hemispheres or deeply etched wells with metal film edges suspended over the etched wells.

In a second aspect, there is provided a metal-coated polymer substrate comprising a nanoarray of depressions, wherein said nanoarray of depressions is substantially free of said metal coating, obtainable by the method defined above. In one embodiment, the polymer substrate of the second aspect is coated with a gold layer.

In a third aspect, there is provided a method of using a metal-coated polymer substrate according to the second aspect for manufacturing bio- and chemical sensors.

In a fourth aspect, there is provided a method of using a metal-coated polymer substrate according to the second aspect for manufacturing color filters.

DEFINITIONS

The following words and terms used herein shall have the meaning indicated:

The term "bulk refractive index sensitivity", as used in the context of the present specification, relates to a measurement of a change in resonant wavelength ($\Delta\lambda$) in relation to a change in the refractive index ($\Delta\eta$). The bulk refractive index sensitivity may be represented by the units $\Delta\lambda/\Delta\eta$ [nm/RIU].

The prefix "nano" as used in the present specification, shall be taken to refer to, unless otherwise specified, structures having width and/or height dimensions between about 1 nm to about 1,000 nm. The prefix "micro" as used in the present specification, shall be taken to refer to, unless otherwise specified, structures having width and/or height dimensions between 1 μm to 500 μm.

The word "substantially" does not exclude "completely" e.g. a composition which is "substantially free" from Y may be completely free from Y. Where necessary, the word "substantially" may be omitted from the definition of the invention.

Unless specified otherwise, the terms "comprising" and "comprise", and grammatical variants thereof, are intended to represent "open" or "inclusive" language such that they include recited elements but also permit inclusion of additional, unrecited elements.

As used herein, the term "about", in the context of concentrations of components of the formulations, typically means +/−5% of the stated value, more typically +/−4% of the stated value, more typically +/−3% of the stated value, more typically, +/−2% of the stated value, even more typically +/−1% of the stated value, and even more typically +/−0.5% of the stated value.

Throughout this disclosure, certain embodiments may be disclosed in a range format. It should be understood that the description in range format is merely for convenience and brevity and should not be construed as an inflexible limitation on the scope of the disclosed ranges. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., well as individual numbers within that range, for example, 1, 2, 3, 4, 5, and 6. This applies regardless of the breadth of the range.

Disclosure of Optimal Embodiments

Exemplary, non-limiting embodiments of a method for forming a polymer substrate with a variable refractive index will now be disclosed.

In one embodiment, there is provided a method of forming a polymer substrate with variable refractive index sensitivity, the method comprising the steps of: (a) contacting a metal-coated patterned mold with a polymer substrate at a temperature sufficient to deform said polymer substrate to thereby deposit a patterned mask of a metal film on the polymer substrate; and (b) etching away portions of said polymer substrate not covered by said patterned mask under conditions to form a region of variable refractive index sensitivity on said polymer substrate.

In one embodiment, the metal-coated patterned mold used in step (a) may comprise an outer surface having an array of depressions disposed thereon, and an inner surface defining the surface area of said depressions.

Prior to contacting step (a), the metal may be coated onto the patterned mold through a physical vapor deposition (PVD) process. In one embodiment, a layer of metal film may be thermally evaporated onto the patterned mold. Other possible PVD processes include, but are not limited to, cathodic arc deposition, sputter deposition and pulsed laser deposition.

The deposited metal film may coat substantially the entire surface area of the patterned mold, including the micro-sized or nano-sized depressions. In one embodiment, the depositing step may comprise thermally evaporating a metal onto the inner surface and outer surface of said patterned mold to form said metal-coated patterned mold.

The etching step (b) may comprise a plasma etching step. The plasma etching step may comprise the use of a mixture of oxygen ($O_2$) gas and tetrafluoromethane ($CF_4$) gas as etchant. The etchant mixture may comprise flow rate ratios of $O_2$:$CF_4$ selected from the group consisting of: 10:1, 9:1, 8:1, 7:1, 6:1, 5:1, 4:1, 3:1, 2:1, 1:1, 1:2, 1:3, 1:4, 1:5, 1:6, 1:7, 1:8, 1:9 and 1:10. In one embodiment, the flow rate ration of $O_2$:$CF_4$ is 3:1.

The plasma etching step may be suitably adjusted to provide conditions for obtaining a region of said polymer substrate having the desired bulk refractive index sensitivity. Preferably, the polymer substrate should exhibit a bulk refractive index sensitivity of from 50-500 nm/RIU, i.e. a change in the refractive index of 1 unit results in a corresponding shift in the measured resonant optical wavelength by 50 to 500 nm. In one embodiment, the polymer substrate prepared using the disclosed method may exhibit a bulk refractive index sensitivity selected from the group consisting of: 50 nm/RIU, 100 nm/RIU, 150 nm/RIU, 200 nm/RIU, 250 nm/RIU, 300 nm/RIU, 350 nm/RIU, 400 nm/RIU, 450 nm/RIU, and 500 nm/RIU. In one embodiment, a polymer substrate fabricated with the disclosed method may exhibit a bulk refractive index sensitivity is at least 400 nm/RIU.

The adjusting step may comprise varying etch duration or concentration of the etchant used or a combination of both. The adjusting step may comprise varying the etch duration from 0 to 5000 seconds. In one embodiment, the etching duration (based on an $O_2$:$CF_4$ ratio of 3:1 and with total etchant flow rate of 16 sccm) may be selected from 30 seconds, 60 seconds, 90 seconds, 120 seconds, 150 seconds, 180 seconds, 210 seconds, 240 seconds, 270 seconds and 300 seconds. In one embodiment, the etching duration may be selected from the group consisting of: 30-300 seconds, 60-300 seconds, 90-300 seconds, 120-300 seconds, 150-300 seconds, 180-300 seconds, 210-300 seconds, 240-300 seconds and 270-300 seconds.

After etching step (b), a partially metal-coated polymer substrate comprising an ordered nanoarray of depressions, wherein the ordered nanoarray of depressions is substantially free of the metal coating may be obtained. This product metal-coated polymer substrate may be used for the manufacture of bio- and/or chemical sensors. In another embodiment, the metal-coated polymer substrate prepared from the above disclosed method may be used for the manufacture of color filters.

In one embodiment, contacting step (a) excludes a step of applying external pressure to compress said metal-coated patterned mold with said polymer substrate. The transfer of the metal film from the mold to the polymer substrate may occur upon contact or due to the weight exerted by the mold on the polymer substrate.

The metal-coated patterned mold may be coated with a metal selected from silver, gold, copper, titanium, and chromium. In one embodiment, the patterned mold is coated with a layer of gold. The gold layer may have a thickness of from about 5 to about 1000 nm. Advantageously, the thickness of the gold layer may be modified in order to provide a desired bulk refractive index sensitivity of the polymer substrate. In one embodiment, the thickness of the gold layer is selected from the group consisting of 5 nm, 10 nm, 50 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm and 1000 nm. In another embodiment, the thickness of the gold layer may be from 5 nm to 500 nm. In another embodiment, the thickness of the gold layer is from about 50 nm, to 150 nm.

The patterned mold may comprise micro- or nano-sized depressions. The depressions may assume any suitable geometric shapes. Exemplary geometric shapes may be selected from, but are not limited to, holes, circle, semi-circles, conical, pyramidal, oval, crescent, star, triangular, and spherical shapes. In one embodiment, the patterned mold comprises nano-sized holes. The nano-sized holes may have nano-hole dimensions of between 10 nm to 1 micrometer in diameter and depth, and a nano-hole periodicity (space between each nano-hole) of between 10 nm to 5 micrometers. In one embodiment, the nanoholes have diameter and depth of about 250 nm.

During the contacting step (a), the metal layer coated on the outer surface of the patterned mold is transferred onto the polymer substrate. However, the metal layer coated on the inner surface of the patterned mold (surface area defined by depressions) is not deposited on said polymer substrate. This results in the formation of a patterned mask on the polymer substrate. In one embodiment, the transferred metal layer may comprise the same thickness as the metal layer when it was coated on the patterned mold. Additionally, during the contacting step (a), the metal-coated patterned mold and the polymer substrate may be contacted under a temperature between 30-1000° C. In one embodiment, the contacting temperature may be selected from the group consisting of 30° C., 60° C., 90° C., 120° C., 150° C.; 200° C., 250° C., 300° C., 350° C., 400° C., 450° C., 500° C., 600° C., 700° C. 800° C., 900° C., and 1000° C. The selected temperature may be dependent on the type of polymer substrate used.

Preferably, the temperature is selected such that the polymer substrate will become deformable. Under the weight of the patterned mold and the elevated temperature conditions, the portions of the polymer substrate contacting the depressions on the mold may deform to assume the geometric shapes of the depressions. Upon contact, the metal layer deposited on the outer surface of the patterned mold may be transferred onto the surface of the polymer substrate. In one embodiment, where the polymer PEAA is used as the polymer substrate, the contacting temperature is selected to be 60° C.

The polymer substrate may be composed of a transparent or translucent polymer. In one embodiment, the polymer substrate may have a glass transition temperature in a range between 30° C. to 1000° C. The polymer substrate may be composed of a polymer selected from the group consisting of: poly(ethylene co-acrylic acid) (PEA), polyvinyl acetate (PVA), polymethyl(meth)acrylate (PMMA), fluorinated ethylene propylene (FEP), polyepoxide and co-polymers thereof. In one embodiment, the polymer substrate is composed of PEAA.

BRIEF DESCRIPTION OF DRAWINGS

The accompanying drawings illustrate a disclosed embodiment and serves to explain the principles of the disclosed embodiment. It is to be understood, however, that the drawings are designed for purposes of illustration only, and not as a definition of the limits of the invention.

FIGS. 1A-1F show a schematic diagram of the process according to an embodiment of the disclosure.

FIG. 2A shows a scanning electron microscopic (SEM) image of the gold-coated PEAA film obtained in Example 1 before etching. FIGS. 2B and 2C show SEM images of the gold-coated PEAA film at etching durations of 90 s and 150 s respectively.

FIG. 12A shows the biotin-functionalized nanohole arrays.

FIGS. 12B to 12D show the UV-Vis spectra of the biotin-functionalized nanohole arrays before and after streptavidin ("SA") binding and at etching durations of 0 s, 90 s and 150 s referred to in Example 5 respectively.

EXAMPLES

Figures 3A, 3B, 3C, 3D:
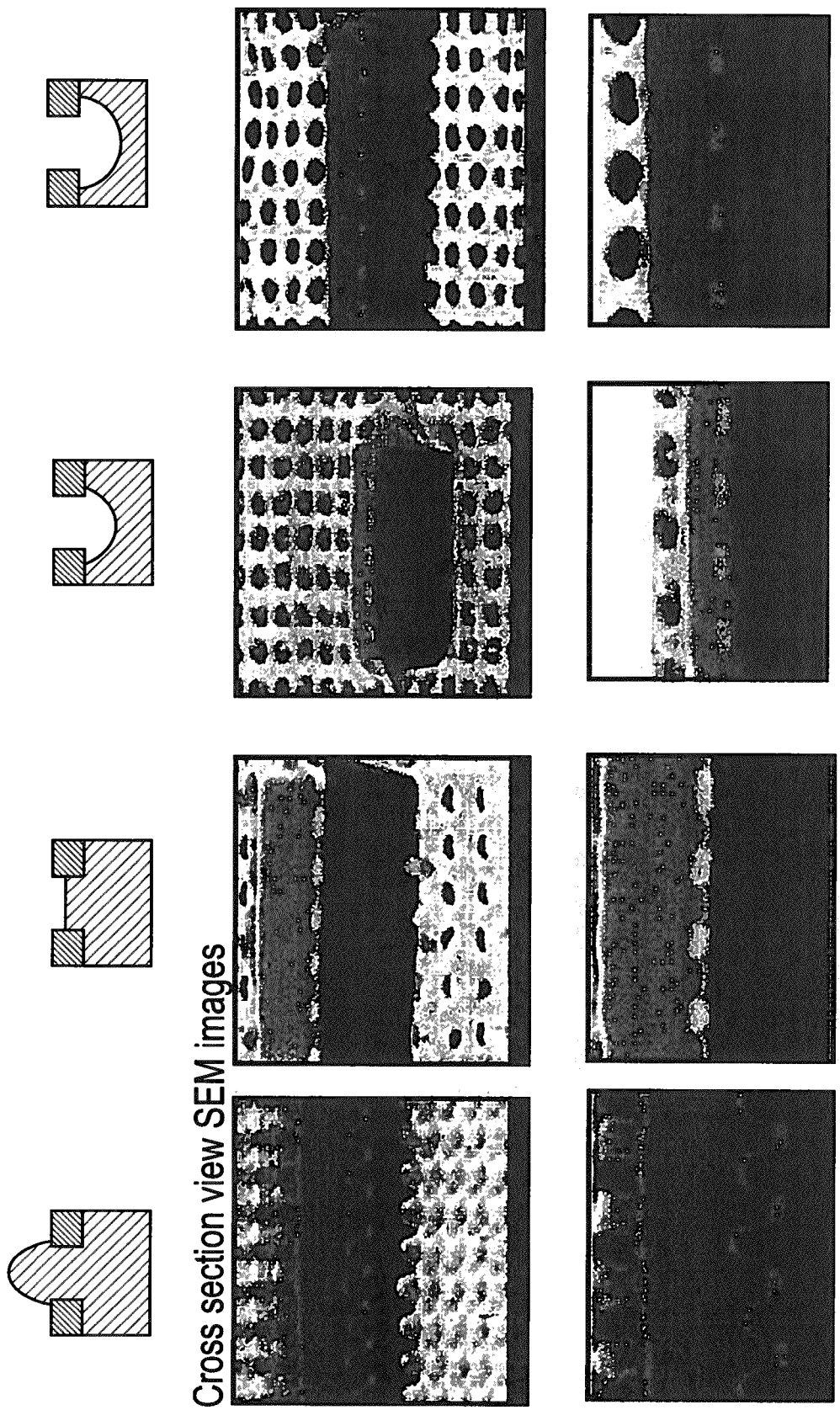
FIG. 3A shows an SEM image of the cross section of the gold-coated PEAA film obtained in Example 1 before etching.
FIGS. 3B to 3D show SEM images of the cross section of the nanoholes of the patterned old-coated PEAA film at etching durations of 30 s, 90 s and 150 s respectively.

Non-limiting examples of the invention will be further described in greater detail by reference to specific Examples, which should not be construed as in any way limiting the scope of the invention.

Example 1

A dimpled silicon mold having on its surface nanoholes of 250 nm in diameter and 250 nm in depth and a periodicity, D, of 420 nm was purchased from NIL Technology, Denmark. The mold had dimensions of 1 cm in length, 0.6 cm in breadth and 0.05 cm in depth. A layer of gold having a thickness of about 50 nm to 150 nm (from Birmingham Metals, United Kingdom (UK)) was thermally evaporated onto the silicon mold at normal incidence to obtain the master mold.

Poly(ethylene-co-acrylic acid) (PEAA) beads (from Sigma-Aldrich Co, Missouri, United States of America (USA)) were heated to 90° C. and pressed flat between two pieces of microscopic glass slides to obtain a thin PEAA film of about 1 mm thick. The PEAA thin film was then allowed to cool down to room temperature.

Thereafter, the gold was transferred from the master mold to the PEAA film in accordance with steps (1) and (2) of the schematic diagram shown in FIGS. 1A-1F.

Referring to FIGS. 1A-1F, the master mold 102 having a gold layer 104 deposited on the surface of the silicon mold as well as on the bottom of the nanoholes was carefully placed onto the PEAA film 106 in accordance with step (1) of FIGS. 1A-1F and slowly heated up to 60° C. Step (1) is also known as a contact printing step. During this step, the PEAA film 106 softened as it was heated up. The evaporated gold layer 104 on the master mold 102 was then able to contact and adhere onto the PEAA film 106 by the weight of only the mold with no external pressure applied, to thereby obtain a gold-coated PEAA film 108. The master mold 102 was then demolded in step (2). However, only the gold layer 104 deposited on the surface of the mold 102 adhered onto the heated and softened PEAA film 106. The gold layer 104 that was evaporated onto the bottom of the nanoholes was not transferred onto the PEAA film 106 Furthermore, dome-shaped nanostructures 110 were formed on the gold-coated PEAA film 108.

A scanning electron microscopic (SEM) image of the gold-coated PEAA film obtained in this example is shown in FIG. 2A, confirming the formation of dome-shaped nanostructures. This is because during the contact printing step, the PEAA polymer was softened near its glass transition temperature of about 80° C. and filled the gold nanoholes of the master mold to thereby form these dome-shaped nanostructures. This is evidenced in FIG. 2A where these nanostructures appear symmetrical and uniform with diameters of about 250 nm, coinciding with the diameter of the master mold nanoholes.

An SEM image of the cross section of the gold-coated PEAA film is shown in FIG. 3A. As mentioned above, except for the weight of the silica master mold, no external pressure was applied. The small weight pressure of the master mold of 0.023 N/cm$^3$, with a silicon wafer density of 2.33 g/cm$^3$, weight of 0.07 grams and volume of 0.03 cm$^3$, resulted in the dome-shaped nanostructures having a uniform height of about 170 nm as measured from FIG. 3A.

Example 2

In this example, the gold-coated PEAA film obtained from Example 1 was plasma etched at different conditions.

Specifically, reactive ion plasma using a reactive ion etching system from Trion Technology, Fla., USA was used to etch the gold-coated PEAA film using $O_2$ and $CF_4$ gases at flow rates of 12 and 4 standard cm$^3$ (sccm) respectively. The reactive power used was 30 W.

The etching was repeated up to 9 times for a duration of 30 s each time in order to achieve different etching durations. Accordingly, the etching durations in this example ranged between 30 s and 270 s.

Steps (4) to (6) of FIGS. 1A-1F show schematically the effect of different etching durations using $O_2$ and $CF_4$ on the gold-coated. PEAA film 108. Referring to FIGS. 1A-1F, step (4) shows the effect of etching after 30 s, step (5) shows the effect of etching after 90 s and step (6) shows the effect of etching after 150 s. It can be seen from step (4) in FIGS. 1A-1F that an etching duration of 30 s completely removed the dome-shaped nanostructures 110 and created nanoholes 112 at the gold layer 104. At an etching duration of 90 s, the nanoholes 112 were enlarged into the PEAA film 106 of the gold-coated PEAA film 108. At an etching duration of 150 s, the nanoholes 112 at the PEAA film layer 106 were further enlarged.

SEM images after etching of the gold-coated PEAA film at a duration of 0 s, 90 s and 150 s are shown in FIGS. 2A to C respectively, confirming the removal, of the dome-shaped nanostructures and the formation of nanoholes in the gold-coated PEAA film. It can be seen in FIGS. 2B and 2C that the nanodomes were chemically removed by etching without affecting the structural integrity of the nanoholes. This evidenced in FIGS. 2B and 2C where the nanoholes in the gold-coated PEAA film have diameters of about 250 nm, coinciding with the diameter of the master mold nanoholes. Accordingly, it can he concluded that the nanohole pattern was successfully replicated from the master mold to the PEAA film with good repetition and quality.

FIGS. 2B and 2C also show that the gold layer of the PEAA film is visibly brighter (i.e. of a lighter colour) than the etched holes due to the higher mass density of gold as compared to the lower mass density of the polymeric PEAA. In addition, the nanoholes were etched through the gold layer and into the PEAA film to a depth lower than the surface gold layer and hence, appear as circular holes with a darker contrast. Accordingly, it is evidenced that this fabrication method in accordance with an embodiment of the invention produces high quality nanohole structures with a well-defined geometrically circular shape.

SEM images of the cross section of the nanoholes of the patterned film at etching durations of 0 s, 30 s, 90 s and 150 s are shown in FIGS. 3A to 3D respectively. Referring to FIGS. 3A to 3D, the dark black colour indicates the PEAA region which previously existed before a trench was etched using focused ion beam (FIB) in order to obtain the cross-section. The dark grey region indicates the platinum that deposited, thereby revealing the interface between air and PEAA polymer.

As seen in FIG. 3A, at 0 s etch time, the dome-shaped polymer structures (black area) at the nanoholes are clearly visible under the grey-colored platinum deposit. Further, the thin film cross-sections of the nanoholes are shown by the evenly spaced out bright horizontal slits.

As seen in FIG. 3B, at 30 s etch time, the nanodomes had completely disappeared but some polymer was still left within the nanoholes as evident by the platinum deposit represented by the grey strips in between the bright horizontal slits.

As seen in FIG. 3C, at 90 s etch time, the nanoholes are etched deeper into the polymer with the grey strips dropping beneath the horizontal slits, which indicates that the edges of the old nanoholes were exposed in air.

Figure 5:
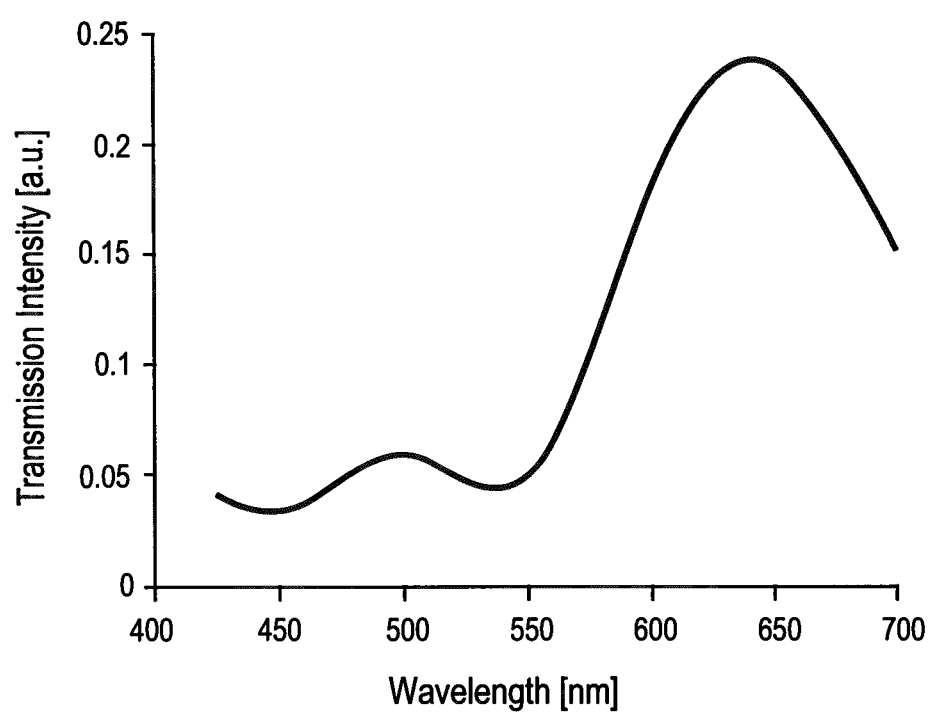
FIG. 5 shows the ultraviolet-visible (UV-Vis) spectrum of a finite difference time domain (FDTD)-simulated free-standing gold film referred to in Example 2.

As seen in FIG. 3D, at 150 s etch time, the gold film is free standing as shown by the grey strips which had infiltrated into the void spaces between the free standing gold film (i.e. the bright horizontal slits) and the PEAA substrate (i.e. the black region). Evidently, as the gold film rested on the PEAA substrate, it is expected that the gold film would still be supported at random positions, not shown in FIG. 3D. However, the patterned film exhibited a predominant characteristic of a free-standing gold film as evident from comparing FIG. 5 with FIGS. 6A and 6B of the experimental and simulated transmission spectrum of a free-standing gold film respectively.

FIGS. 3A to 3D confirm that the nanodomes can be easily removed by reactive plasma etching. By simply controlling the etching time of 0, 30, 90 and 150 s, it is shown that the extent of polymer filling at the nanohole entrance can be controlled, thereby resulting in flat bottom nanoholes (as seen in FIG. 3B at an etching duration of 30 s), holes with curvatures (as seen in FIG. 3C at an etching duration of 90 s), until a free-standing (or suspended) film is obtained around the holes (as seen in FIG. 3D at an etching duration of 150 s).

The different nanohole structures in the gold-coated PEAA film have different refractive index sensitivities. In terms of optical measurement, the transmission spectra of the nanoholes created in the gold-coated PEAA polymer substrate were measured using a ultraviolet-visible (UV-Vis) spectrometer (from Perkin Elmer, Inc., Massachusetts, USA). The non-polarized light was incident normally from the PEAA polymer substrate and scanned from 400 nm to 1000 nm to measure the transmission spectra.

Optical images of the patterned gold film taken at different etching durations of 0 s, 30 s, 90 s, 150 s-210 s and 270 s by a microscope (Nikon 5200, Nikon Corporation, Japan) using a 10× magnification lens are shown in FIGS. 4A to 4F respectively.

Figure 4A:
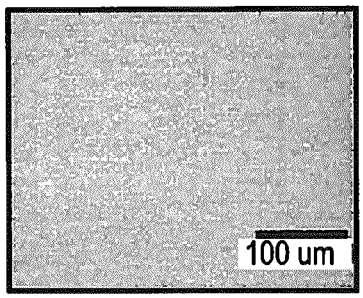
FIGS. 4A to 4F show optical images of the patterned gold film taken at etching durations of 0 s, 30 s, 90 s, 150 s, 210 s and 270 s respectively in Example 2.
Figure 4B:
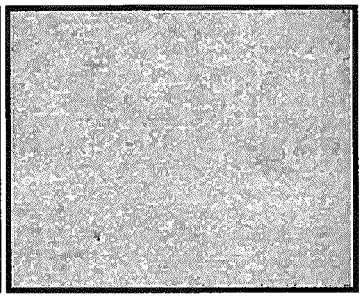

FIGS. 4A and 4B show that the patterned film after etching durations of 0 s and 30 s had an overall pink colour. As evidenced above and in FIG. 2A, the patterned film still had a majority of the nanoholes covered by the dome-shaped nanostructures on its surface at etching durations of 0 s and 30 s. Accordingly, the overall pink colour in FIGS. 4A and 4B is due to the weak transmission peak at $\lambda_{Au-PEAA}(1,1)$ of 600 nm shown in the UV-Vis spectra of the film at etching durations of 0 s and 30 s shown in FIGS. 6A and 6B. A transmission peak at 600 nm coincides with the wavelength of orange to red colours in the electromagnetic spectrum of visible light.

Figure 7:
FIG. 7 shows the range of wavelengths for visible light as a colour reference.

For ease of reference, FIG. 7 shows the range of wavelengths for visible light as a colour reference.

Figure 4C:
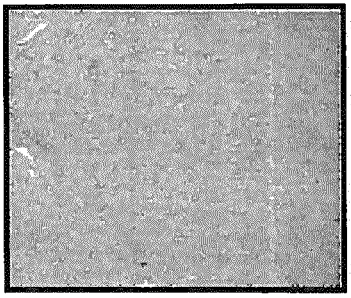
Figure 4D:
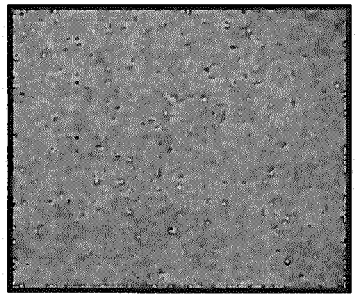
Figure 4E:
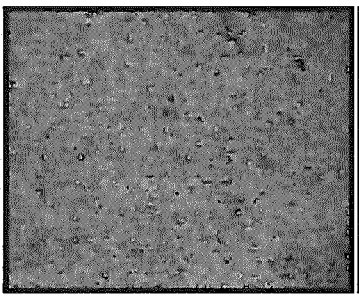
Figure 4F:
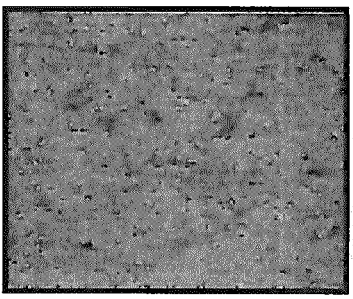
Figure 6A:
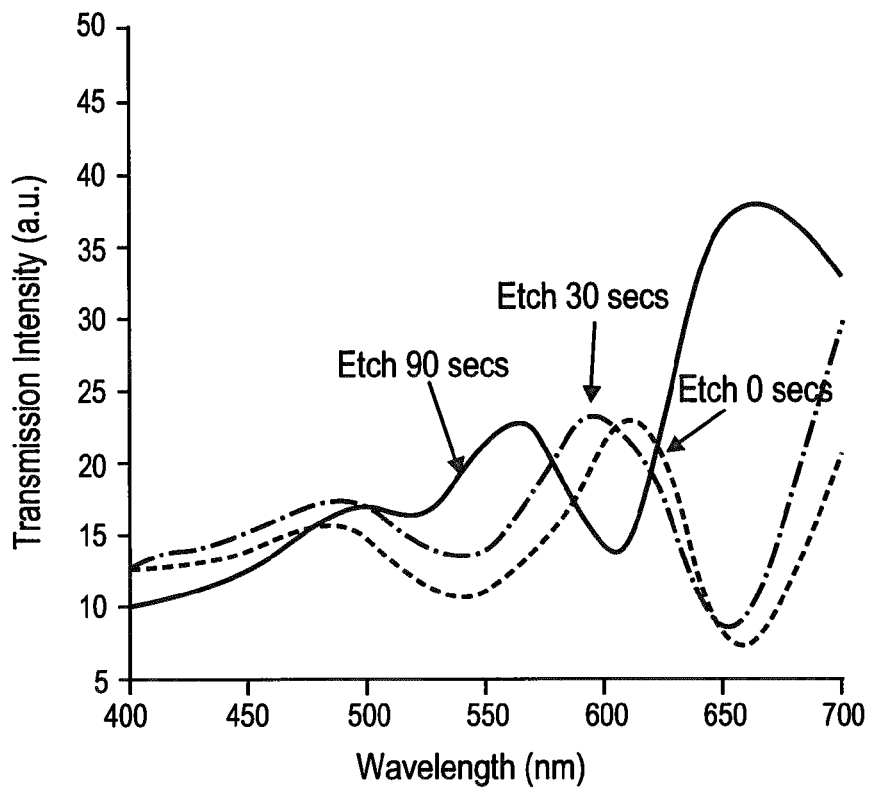
FIGS. 6A and 6B show the UV-Vis spectrum of the patterned film at etching durations of 0 s, 30 s, 90 s, 150 s, 210 s and 270 s referred to in Example 2.
Figure 6B:
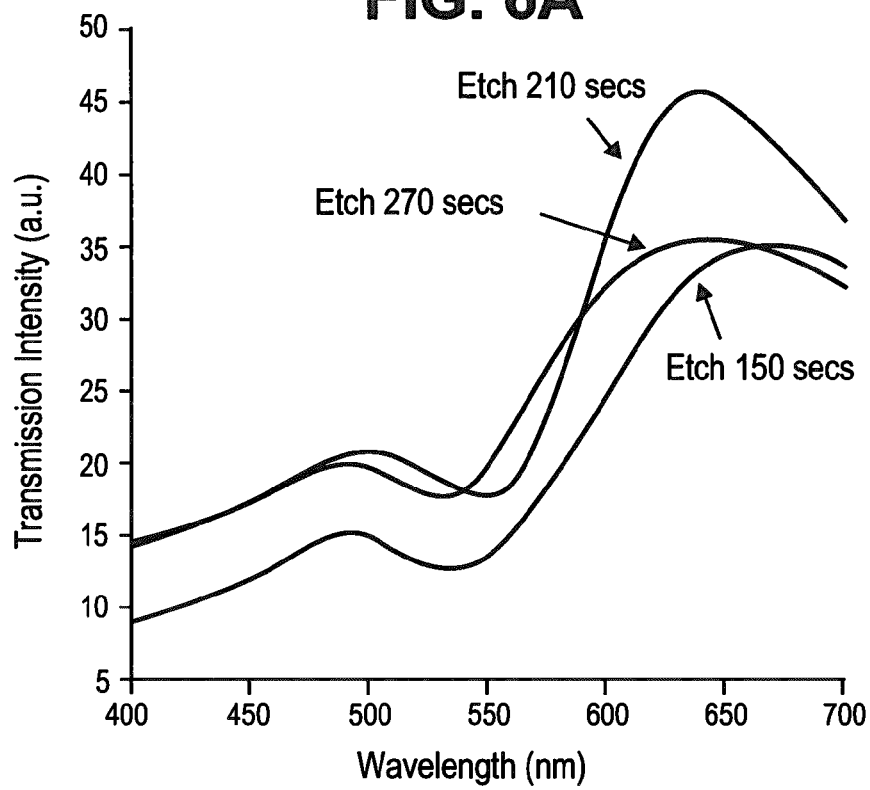

FIGS. 4D to 4F show that the patterned film after etching durations of 150 s, 210 s and 270 s had an overall red colour, which is due to the transmission peak at $\lambda_{Au-Air}$ at the Au-Air interface of 650 nm shown in FIGS. 6A and 6B. Without being bound by theory, the gold layer on the patterned PEAA film at etching durations of 150 s, 210 s and 270 s is believed to exist as a free-standing film around the nanoholes, supported by the PEAA substrate.

The finite difference time domain (FDTD) simulations of light transmitting through isolated nanoholes or arrays of nanoholes demonstrated in the following Example 3 supported the theory of a free-standing gold nanohole film.

FIG. 4C shows that the patterned film after n etching duration of 90 s had an overall orange colour due to two transmission peaks, namely a weak yellow peak at $\lambda A_{Au-PEAA}(1,1)$ of 560 nm and a strong red peak at $\lambda_{Au-Air}$ of 650 nm as shown in FIGS. 6A and 6B. This shows that the patterned film after an etching duration of 90 s existed as a mixture between a free-standing gold film (i.e. the film at etching durations of 150 s, 210 s and 270 s) and incomplete etching of the nanodomes (i.e. the film at etching durations of 0 s and 30 s). Further, a visible tinge of a green streak in FIG. 4C was due to the peak at $\lambda_{Bulk\ Au}$ of 500 nm. It is to be noted that the peak at $\lambda_{Bulk\ Au}$ of 500 nm existed in all the UV-Vis spectra of FIGS. 6A and 6B.

In addition, beyond the visible range of 700 nm, there exists another peak at $\lambda_{Au-PEAA}(1,1)$ of 750 nm as will be shown later in Example 4 and FIGS. 9A to 9D and 10A to 10D.

Example 3

In this example, finite difference time domain (FDTD) simulations of light transmitting through isolated nanoholes or arrays of nanoholes were performed.

The commercial software Optiwave FDTD (from Optiwave, Canada) was used to simulate the nanoholes in 3D. The FDTD method was used to calculate the 3D electric field distribution of arrays of nanoholes in a gold film upon irradiation with a continuous broadband plane wave light source. The dispersion of the gold film was modeled using a Drude/Lorentz model.

Figure 8:
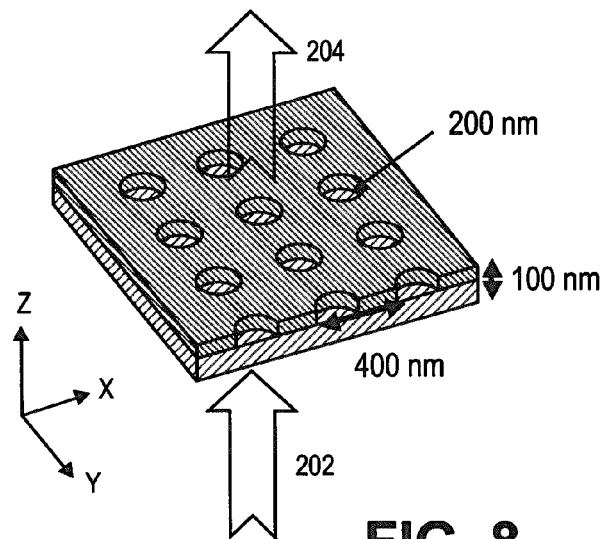
FIG. 8 shows a schematic diagram of the 3D nanohole structure used for the FDTD simulation in Example 3.
Figure 9A:
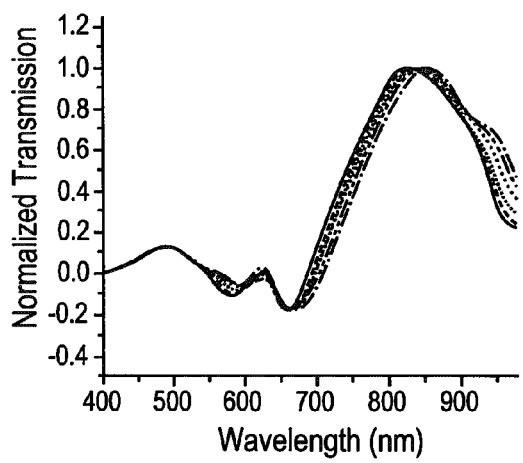
FIGS. 9A to 9D show the UV-Vis spectra of the nanohole arrays after etching durations of 0 s, 30 s, 90 s and 150 s placed in varying weight concentrations of glycerol-water solutions referred to in Example 4 respectively.
Figure 9B:
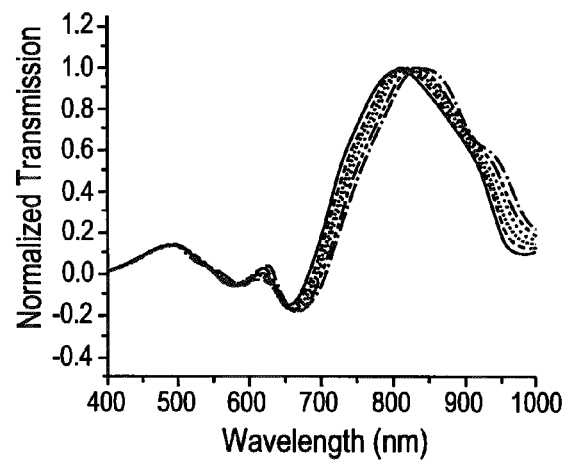
Figure 9C:
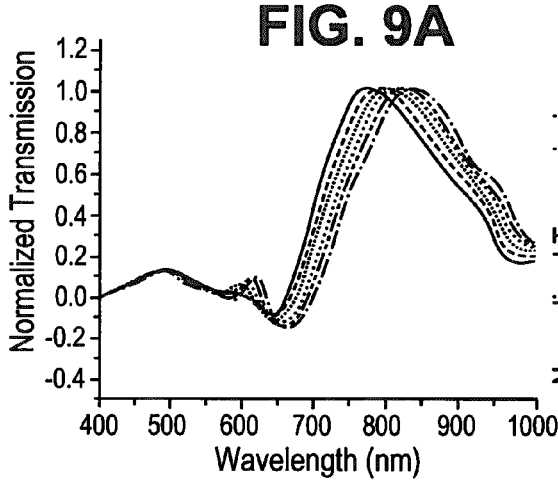
Figure 9D:
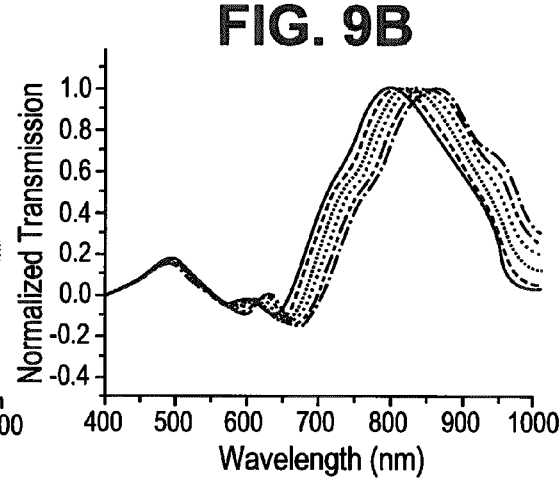

A schematic diagram of the 3D nanohole structure used for the FDTD simulation in this example is shown in FIG. 8. The unit cell was a single hole with periodic boundary conditions applied to the x and y directions to describe an infinite square array and uni-axial perfectly matched layers along the z direction. The dimensions chosen for the simulations were measured from the SEM image shown in FIGS. 2a to 2C. Referring to FIG. 8, the periodicity used was 400 nm, the thickness of the gold film used was 100 nm and the hole diameter used was 200 nm. The refractive index of the PEAA substrate is 1.5. The circularly polarized light source was placed behind the glass and incident in the direction shown by arrow 202. The x-y plane monitors were placed at a far-field to collect the transmitted spectrum exiting in the direction shown by arrow 204. The amplitude of incident, electric field was 1 volts/meter (V/m).

As mentioned above in Example 2, the simulation results supported the theory of a free-standing gold nanohole film. Specifically, the simulated UV-Vis curve shown in FIG. 5 coincided with the profile of the UV-Vis curves of etching durations of 150 s, 210 s and 270 s shown in FIGS. 6A and 6B of the patterned film of Example 2, It is to be appreciated that etching durations of 150 s, 210 s and 270 s was when a free-standing gold film was obtained. The simulations in this example thus corroborate the experimental results in Example 2.

Example 4

In this example, the localized surface plasmon resonance (LSPR) properties of the patterned film obtained from Example 2 were characterized.

The UV-Vis spectra of the nanohole arrays after etching durations of 0 s, 30 s, 90 s and 150 s placed in varying weight concentrations of glycerol-water solutions were obtained and are shown in FIGS. 9A to 9D respectively.

Figure 10A:
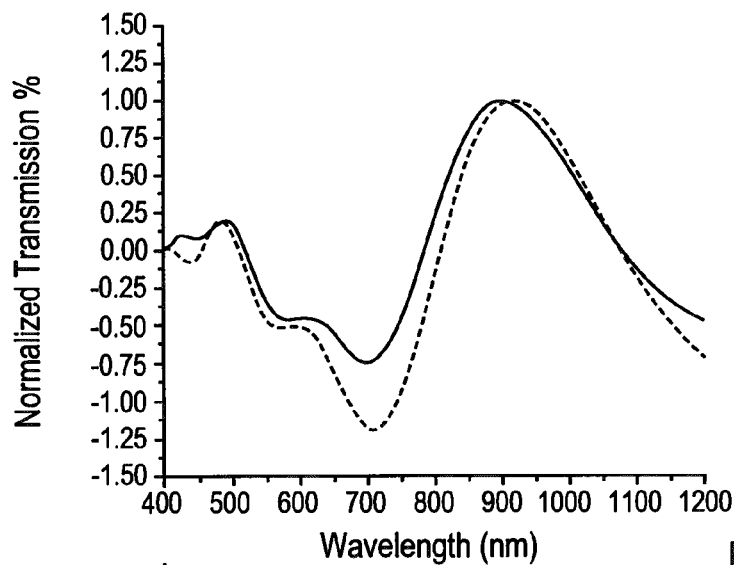
FIGS. 10A to 10C show the UV-Vis spectra of the FDTD-simulated nanohole arrays of 100 nm in thickness after etching durations of 0 s, 90 s and 150 s placed in varying weight concentrations of glycerol-water solutions referred to in Example 4.
Figure 10B:
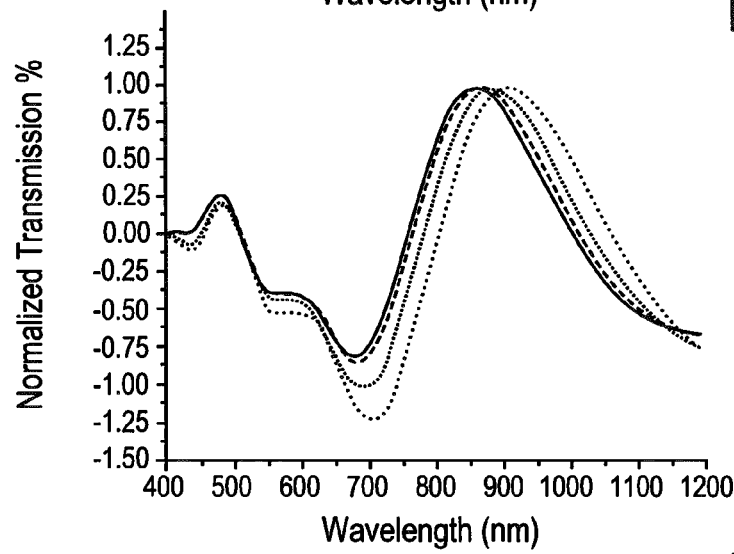
Figure 10C:
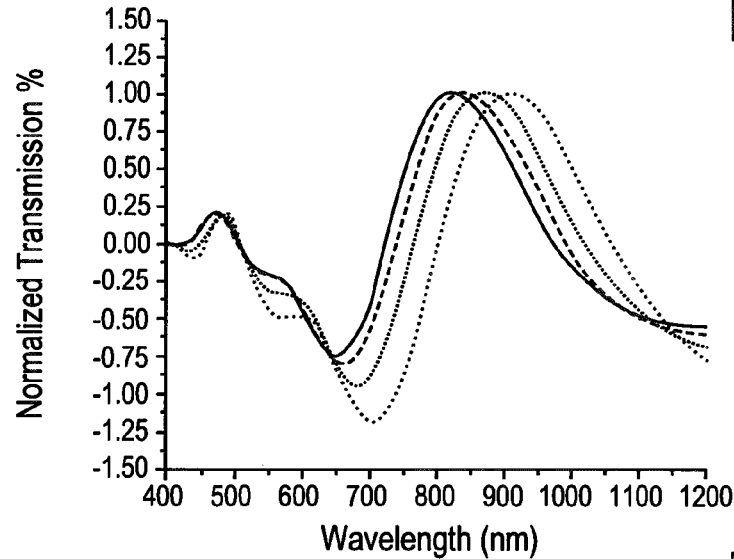

The UV-Vis spectra of the FDTD-simulated nanohole gold film arrays of 100 nm in thickness after etching durations of 0 s, 90 s and 150 s placed in varying weight concentrations of glycerol-water solutions are also shown in FIGS. 10A to 10C, in accordance with the method of Example 3.

In each figure, glycerol of 0 wt % to 100 wt % water solution is shown from left to right.

Referring to FIGS. 9A to 9D and 10A to 10C, three plasmon peaks were obtained in the UV-Vis spectra. The first peak of the plasmon resonance at around $\lambda_{Bulk\ Au}$ of 500 rim was observed for all spectra for bulk gold. The infinite nanohole arrays exhibited peaks that are characteristic of Surface Plasmon Polariton (SPP)-Bloch waves (BW) at $\lambda_{Au\text{-}PEAA}(1,0)$ of 750 nm and $\lambda_{Au\text{-}PEAA}(1,1)$ of 600 rim, where (1,0) and (1,1) are integer pairs that define the particular order of the SPP-BW in good agreement with literature. The minima at around 690 nm and around 570 nm are associated with Wood's anomalies.

In a glycerol solution of different concentrations, it is expected for an infinite Au film with nanohole arrays from literature that the SPP-BW peaks shift to longer wavelengths as the refractive index, n, is increased, i.e. as the concentrations of the glycerol solution increase. The bulk gold plasmon peak at 500 nm, however, would remain unchanged. Furthermore, the degree of the SPP-BW peak shift, increases with the increase of etching time. This is corroborated by the FDTD results in FIGS. 10A to C.

The experimental results shown in FIGS. 9A to D are also in good agreement with the FDTD results in FIGS. 10A to C.

The refractive index sensitivities were then measured for gold film arrays with varying thicknesses of 75 nm, 100 nm, 125 nm and 150 nm and different etching durations.

Figure 11:
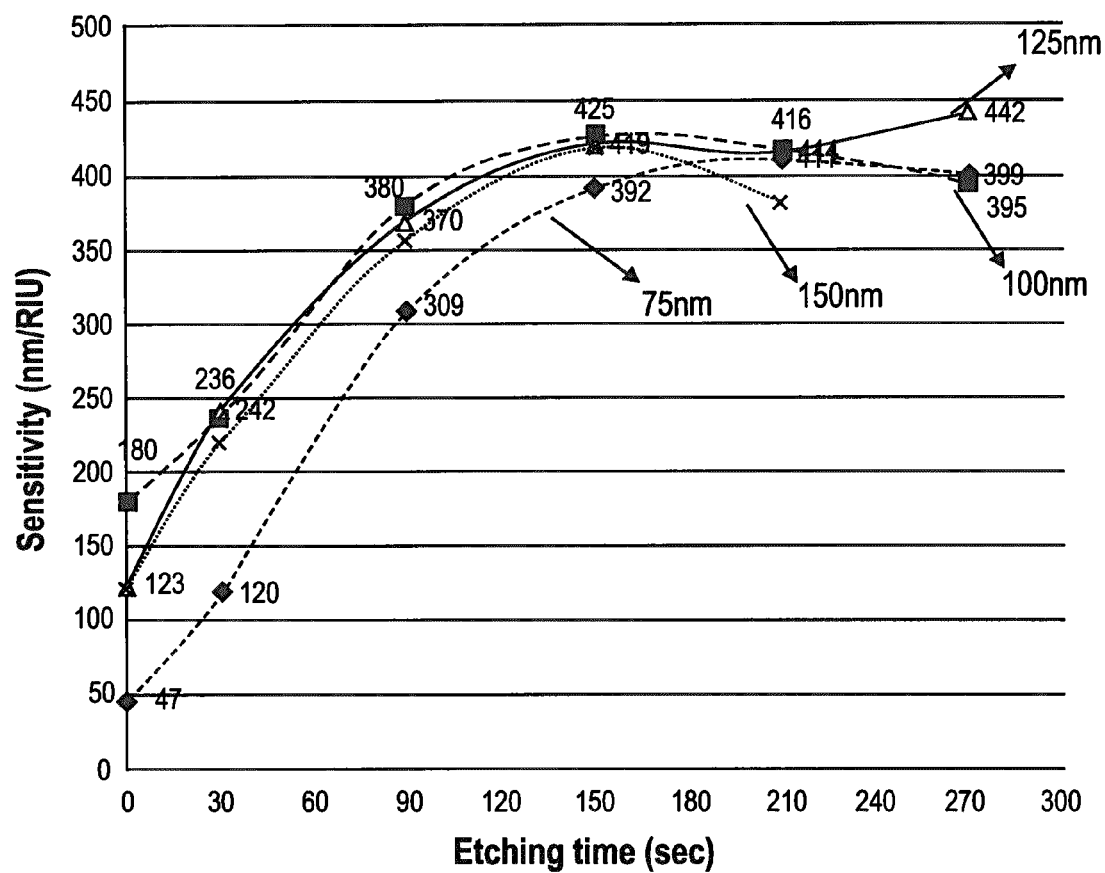
FIG. 11 shows a graph of refractive index sensitivities in nm/refractive index unit (RIU) against etching time for different film thicknesses of 75 nm, 100 nm, 125 nm and 150 nm referred to in Example 4.

The graph of refractive index sensitivities against etching time for the different film thicknesses are shown in FIG. 11. Referring to FIG. 11, the results show that post etching can enhance the refractive index sensitivity and this effect is maximized at the etching time of 150 s.

It is known from literature that the origin of extraordinary optical transmission, EOT, is a result of LSPR excited at the nanoholes. As the excitation of LSPRs is known to be sensitive to the refractive index of the surrounding medium, the presence of nanodomes in the vicinity of nanoholes is expected to strongly influence the excitation of LSPR and the peak wavelengths at which EOT is observed.

Furthermore, in FIG. 3A, the nanodomes can be seen to block the nanohole entrance where localised plasmonic fields are expected to be strongest.

It is evidenced in FIG. 11 that without etching, i.e. at an etching time of 0 s, the presence of nanodomes at the nanohole entrance strongly degraded the sensitivity of the sensitivity sensor, resulting in a bulk sensitivity value of about 50 nm/refractive index units (RIU) for a 75 nm thick gold film, about 100 nm/RIU for a 100 nm gold film and about 175 nm/RIU for a 125 nm gold film.

Furthermore, as etching time increased from 0 s to 30 s and then to 90 s, it can be observed from FIG. 11 that bulk sensitivity increased steeply and almost linearly with etching time. Without being bound by theory, the reason for this relationship between etching time and bulk sensitivity is believed to be because of the different extent of polymer coverage at the nanoholes.

Still referring to FIG. 11, beyond an etching time of 150 s, bulk sensitivity reached a plateau at about 400-420 nm/RIU for all three thicknesses. This final sensitivity is in good agreement with the theoretically estimated value of 420 nm/RIU due to the geometrical periodicity of 420 nm.

The good agreement between the measured and theoretical bulk sensitivities provides evidence that, through an embodiment of the method disclosed herein, the gold layer was transferred from the master mold to the PEAA substrate and retained the nanoholes with high fidelity, as also seen in the SEM images in FIGS. 2A to 2C. In addition, through exploiting the leaking of PEAA polymer followed by a plasma etching process, it is demonstrated that the bulk sensitivity can be controllably tuned such that it can be initially reduced and then restored to its original theoretical value.

Example 5

In this example, three different substrates were used. The first was with an as-transferred gold film, i.e. no etching, the second was with curved nanoholes, i.e. etched for 90 s, and the third was with a suspended nanohole gold film, i.e. etched for 150 s.

The substrate with a nanohole array in the gold film was drop-coated with a biotin-containing thiol solution to introduce biotin residues to cover the full gold area.

Figure 13:
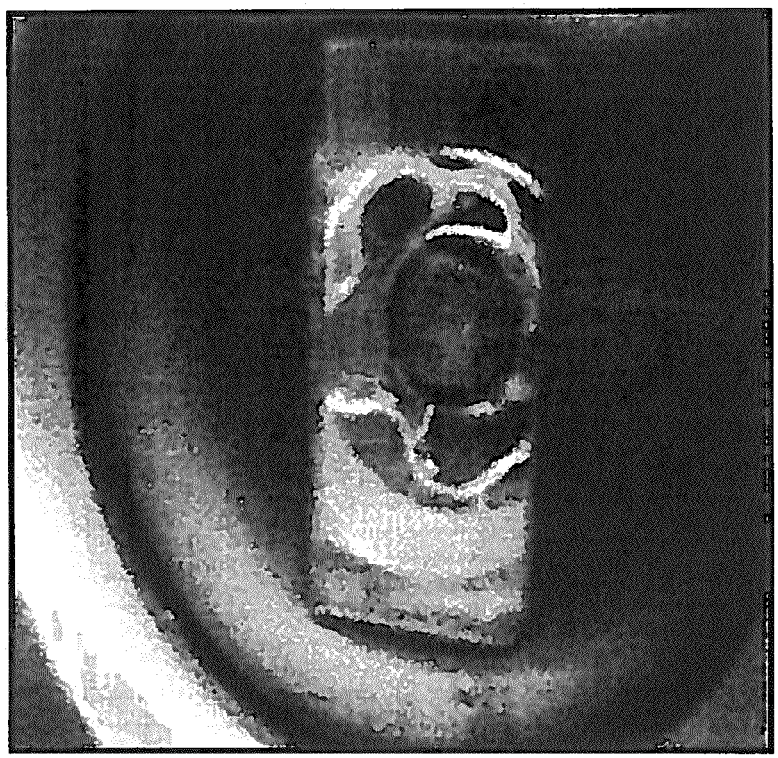
FIG. 13 shows a photograph of a film substrate obtained in accordance with an embodiment of the disclosure integrated into a microfluidic flow cell and used in Example 5.

The substrates were then integrated into a microfluidic flow cell respectively. An example of a microfluidic flow cell is shown in FIG. 13.

After 3 hrs, the UV-Vis sensor was rinsed copiously with water and ethanol and blown dry with $N_2$ gas. The UV-Vis spectrum of the biotin-functionalized sensor was measured in air. Then, 0.1 mg/ml of streptavidin was drop-coated onto the gold surface for 30 minutes. The biotin-streptavidin-functionalized substrate was then rinsed copiously with water and ethanol and blown dry with $N_2$ gas. The UV-Vis spectrum of the resultant substrate was measured in air. The UV-Vis spectra of the biotin-functionalized nanohole arrays before and after streptavidin ("SA") binding and at etching durations of 0 s, 90 s and 150 s are shown in FIGS. 12B to D respectively.

As seen in FIGS. 12B to D, streptavidin binding causes the spectra to shift to longer wavelengths and binding-induced wavelength shift increases with the increase of etching time due to the improvement in sensitivity as a result of longer etching time.

APPLICATIONS

In the present disclosure, there is disclosed a method for high-throughput and large-scale fabrication of gold nanohole arrays based on a CP technique coupled with a post-printing etch step to optimize the nanohole structures for improved plasmonic sensing with maximized refractive index sensitivity.

Specifically, the presently disclosed method offers the following technical and commercial benefits:

1) Cost-effectiveness, large area (cm-scale) fabrication of ordered nanohole arrays. Advantageously, having a large sensing area allows different samples to be drop-coated, thus enabling multiplexing. Additionally, a large area also improves the signal-noise ratio;

2) High throughput production due to the simple fabrication steps achievable under normal lab-environment;

3) Maximised bulk refractive index sensitivity (the disclosed etching step can be adjusted to ensure highest sensitivity is achieved);

4) Fabricated polymer substrates may comprise pseudo-free/freely-supported standing metal film resulting in higher EDT intensity and enlarged biosensing area;

5) Tunable bulk refractive index sensitivity (adjustable sensitivity by varying etching time to suit different dye excitation);

6) Tunable peak wavelength (adjustable wavelength by varying the metal film thickness to suit different applications e.g. different dye excitation wavelengths); and 7) Simple contact-printing step to transfer nanostructures onto a polymer substrate and maximizing the refractive index sensitivity through a short reactive ion plasma etching step.

With the combination of the printing and post-print etching, the present disclosure provides a SPR polymer substrate structure comprising an ordered array of nanohole coated with a metal film, e.g. a gold film. Using the disclose method, it is possible to provide a SPR structure having tunable wavelength and maximized bulk refractive index sensitivity (>400 RIU/nm).

It will be apparent that various other modifications and adaptations of the invention will be apparent to the person skilled in the art after reading the foregoing disclosure without departing from the spirit and scope of the invention and it is intended that all such modifications and adaptations come within the scope of the appended claims.

The invention claimed is:

1. A method of forming a polymer substrate with variable refractive index sensitivity, the method comprising:
    (a) contacting a metal-coated patterned mold with a polymer substrate at a temperature sufficient to deform said polymer substrate to thereby deposit a patterned mask of a metal film on the polymer substrate; and
    (b) etching away portions of said polymer substrate not covered by said patterned mask under conditions to form a region of variable refractive index sensitivity on said polymer substrate.

2. The method of claim 1, wherein said metal-coated patterned mold comprises an outer surface having an array of depressions disposed thereon, and an inner surface defining the surface area of said depressions.

3. The method of claim 1, wherein the method further comprises, prior to contacting depositing a metal layer on said patterned mold via a physical vapour deposition process.

4. The method of claim 3, wherein said depositing comprises thermally evaporating a metal onto the outer surface of said patterned mold.

5. The method of claim 1, wherein said etching comprises a plasma etching.

6. The method of claim 5, wherein said plasma etching further comprises an adjusting to provide conditions for obtaining a desired bulk refractive index sensitivity of said polymer substrate, wherein said adjusting comprises varying etch duration or concentration of etchant used or a combination of both.

7. The method of claim 6, wherein said plasma etching comprises varying the etch duration from 0 to 5000 seconds.

8. The method of claim 1, wherein said metal-coated patterned mold is coated with a metal selected from: silver, golf, copper, titanium, and chromium.

9. The method claim 1, wherein said patterned mold is coated with a layer of gold.

10. The method of claim 9, wherein said gold layer has a thickness of 5-1000nm.

11. The method of claim 1, wherein said patterned mold comprises micro- and nano-sized depressions.

12. The method of claim 1, wherein during said contacting, the metal-coated patterned mold and the polymer substrate are contacted at a temperature in a range of 30° C. to 1000° C.

13. The method of claim 1, wherein said polymer substrate is a transparent or translucent polymer.

14. The method of claim 13, wherein said polymer substrate has a glass transition temperature in a range between 30° C. to 1000° C.

15. The method of claim 14, wherein said polymer substrate is composed of a polymer selected from the group consisting of: poly (ethylene co-acrylic acid) (PEAA), polyvinyl acetate (PVA), polymethyl (meth) acrylate (PMMA), fluorinated ethylene propylene (FEP), polyepoxide and co-polymers thereof.

16. The method of claim 15, wherein said polymer substrate is PEAA.

17. The method of claim 1, wherein said etching is performed under conditions to provide a region having a bulk refractive index sensitivity of from 50 nm/RIU to 500 nm/RIU on said polymer substrate.

18. The method of claim 1, wherein said etching is performed under conditions to provide free-standing metal films on said polymer substrate.

* * * * *